United States Patent [19]
Murrer et al.

[11] Patent Number: 6,001,826
[45] Date of Patent: Dec. 14, 1999

[54] CHEMICAL COMPOUNDS

[75] Inventors: Barry A Murrer, Reading, United Kingdom; David A Schwartz, Exton, Pa.

[73] Assignee: AnorMed, Inc., Langley, Canada

[21] Appl. No.: 07/915,871

[22] Filed: Jul. 20, 1992

Related U.S. Application Data

[60] Continuation of application No. 07/677,411, Mar. 29, 1991, abandoned, which is a division of application No. 07/454,418, Dec. 21, 1989, Pat. No. 5,021,409.

[51] Int. Cl.$^6$ .................. A61K 31/555; A61K 31/34
[52] U.S. Cl. ................................. 514/183; 514/474
[58] Field of Search ................. 514/183; 540/474

[56] References Cited

U.S. PATENT DOCUMENTS

| | | | |
|---|---|---|---|
| 4,156,683 | 5/1979 | Lehn | 260/338 |
| 4,959,210 | 9/1990 | Smiles et al. | 424/85.7 |

OTHER PUBLICATIONS

Zimenkouski, CA 88:105292s (1978).
William, CA 96:97239c (1982).
Rowall, CA 107:112499d (1982).
107 CA:167695v Ciampolini et al. 1987.
99 CA:49518h Kmura et al. 1983.
Campolini et al. 1987, Inorganic Chemistry vol. 26 #21, pp. 3527–3533.
Barefield et al., J.C.S. Chem. Comm., "Characterization Of 2,2'-Bi-(1,4,8,11-tetra-azacyclotetradecane):, etc.,", pp. 302–304 (1981).
Fabbrizzi et al., Inorganic Chemistry, vol. 25, No. 16, "Communications", pp. 2671–2672, copyright by the American Chemical Society (1986).

*Primary Examiner*—Russell Travers
*Attorney, Agent, or Firm*—Morrison & Foerster, LLP

[57] ABSTRACT

Pharmaceutical compositions containing as active ingredients a linked cyclic compound of the general formula I $$Z-(A)_n-Y \qquad (I)$$

in which Z and Y are independently cyclic polyamine moieties having from 9 to 32 ring members and from 3 to 8 amine nitrogen atoms in the ring, A is a linking atom or group, and n is O or an integer from 1 to 6, are indicated for the treatment of viral infections, and preventative administration, especially for retroviral infections.

3 Claims, No Drawings

CHEMICAL COMPOUNDS

This is a continuation of application Ser. No. 07/677,411, filed on Mar. 29, 1991, which was abandoned upon the filing hereof which is a division of Ser. No. 07/454,418, filed Dec. 21, 1989, now U.S. Pat. No. 5,021,409.

This invention concerns improvements in chemical compounds, more especially it concerns compounds and pharmaceutical compositions. In particular it concerns compositions and compounds having activity in in vitro tests on Human Immunodeficiency Virus-infected cells.

The disease known as Acquired Immune Deficiency Syndrome (AIDS) caused by infection by HIV has attracted immense research effort because of the effects of the disease on infected individuals and the dangers of the disease spreading to a wider section of the population. In general, although various chemo-therapeutic treatments have been advocated, and some compounds have emerged as a potential basis for treatment, there is still a need for alternatives. In particular, most treatments such as the compound known as AZT have a high toxicity to cells, and it would be desirable to find compounds which are less toxic. In man, the development of resistance to AZT has been identified as an additional clinical problem.

We have found a group of compounds which show protective properties in in vitro screens of cells challenged with HIV-1 and/or HIV-2, and are therefore indicated as having potential for the treatment of AIDS and AIDS Related Complex and other viral and especially retroviral infections. Accordingly, the present invention provides the use of compounds defined below, in pharmaceutical compositions for treating HIV-infected patients. The invention further provides pharmaceutical compositions comprising a said compound in combination or association with a pharmaceutically acceptable diluent or excipient, for the treatment of HIV-infected patients. The invention nay also be defined as the use of a said compound for the manufacture of a medicament for the treatment of HIV-infected patients. The invention further provides a process for the production of a pharmaceutical composition for the treatment of a HIV-infected patient, comprising the combination of a compound as defined below with a pharmaceutically acceptable diluent or excipient, and formulating said composition into a form suitable for administration to said patient. The invention also provides a method of treatment of an HIV-infected patient, comprising administering to said patient an effective dose of a said compound. It is to be understood that treatment includes prophylactic treatment of patients at risk, in view of the protective properties observed. Whilst this description is especially directed to combatting HIV, this invention includes other aspects in which other diseases may be treated, including for example microbial infections.

A 2,2'-dimer of cyclam has been reported as being isolated as a 2% by-product in the synthesis of cyclam (1,4,8,11-tetraazacyclotetradecane) (Barefield et al, J. C. S. Chem. Comm. (1981), 302). This compound was stated to be insoluble in water. We believe that the insoluble 2,2'-bicyclam is a mixture of the 2R,2'R and 2S,2'S enantiomers; we have characterised a soluble dimer which we believe to be the meso 2R,2'S isomer. The 6,6'-bicyclam isomer has been reported by Fabbrizi et al, Inorg. Chem. 25, 2671 (1986). Certain N,N'-linked bicyclic compounds have been reported by Ciampolini et al, Inorg. Chem. 26, 3527 (1987). No biological activity has been suggested for such compounds.

The present invention provides as active compounds linked cyclic compounds of the general formula I

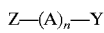

$$Z-(A)_n-Y \qquad (I)$$

in which Z and Y are independently cyclic polyamine moieties having from 9 to 32 ring members and from 3 to 8 amine nitrogen atoms in the ring, A is a linking atom or group, and n is O or an integer from 1 to 6. The invention also encompasses acid addition salts and metal complexes of the compounds of formula I.

In the above formula, A may be alkylene, or a group selected from aryl, fused aryl, polyoxoethylene, carboxylate, esters and amides, or a nitrogen or sulphur atom.

The cyclic polyamine moieties may be substituted or unsubstituted, and suitable substituents are alkyl and/or aryl groups, e.g. of up to 10 carbon atoms, and any other atoms or groups which do not substantially adversely affect the activity or toxicity of the compounds. Preferred moieties are those of 10 to 24 ring members, especially 12 to 18 ring members, and preferred numbers of amine nitrogen atoms are 4 to 6. It is convenient that the moieties are identical. The moieties may be linked by attachment to the carbon atoms or nitrogen atoms of the ring, ie C-C, N-N, C-N.

A number of the active compounds according to the invention are known, and the compounds may be prepared by identical methods or methods analogous thereto.

The compounds are indicated for the treatment of viral infections, especially retrovirus infections and particularly HIV infections, and the compounds of formula I are to be be considered as active compounds for the pharmaceutical compositions, processes for making the same and methods of treatment mentioned above. In these aspects of the invention, it is to be understood that meso forms, enantiomers and resolved optically active forms of the compounds of formula I, are included. Also, it is to be considered within the invention, compounds of formula I diluted with non-toxic or other active substances. Acid addition salts, for example hydrochlorides, and non-toxic labile metal complexes of the compounds of formula I are also active compounds according to the present invention. Non-toxic in the present context has to be considered with reference to the prognosis for the infected patient without treatment. Zinc and nickel complexes are especially indicated, whereas less labile metal atoms such as cobalt and rhodium are less preferred because of likely lower selectivity.

The invention will now be described by way of example only. Characterised samples of 2,2'-bicyclam and 6,6'-bicyclam were tested in the standard in vitro tests, described below.

The compounds of the invention were tested in a screen by the MTT method (J.Virol. Methods 120: 309–321 [1988]). MT-4 cells ($2.5 \times 10^4$/well) were challenged with HIV-1 (HTLV-IIIB) or HIV-2 (LAV-2 ROD) at a concentration of 100 $CCID_{50}$ and incubated in the presence of various concentrations of the test compounds, which were added immediately after challenge with the virus. After 5 days culture at 37° C. in a $CO_2$ incubator, the number of viable cells was assessed by the MTT (tetrazolium) method. Antiviral activity and cytotoxicity of the compounds are expressed in the table below as $ED_{50}$ (ug/ml) and $CD_{50}$ (ug/ml), respectively. The potential therapeutic usefulness was assessed by calculating a Selectivity Index (SI) corresponding to the ratio of $CD_{50}$ to $ED_{50}$. A control test was performed using the known anti-HIV treatment AZT, and a number of comparison compounds were also run through the screen as detailed below.

In the table below, the compounds screened were

A cyclam, recrystallised (comparison only)

B meso (2R,2'S; 2S,2'R) bicyclam plus inactive diluent
C 2R,2'R; 2S,2'S bicyclam racemate. 8HCl
D 6,6'-bicyclam. 8HCl. 2H$_2$O

TABLE

| Compound | Virus | CD$_{50}$ | ED$_{50}$ | SI |
|---|---|---|---|---|
| A | HIV-1 | 226 | >500 | <1 |
|  | HIV-2 | 266 | 54 | 5 |
| B | HIV-1 | 298 | 0.21 | 1435 |
|  | HIV-2 | 299 | 0.32 | 928 |
| C | HIV-1 | 172 | 0.12 | 1430 |
|  | HIV-2 | 200 | 0.62 | 322 |
| D | HIV-1 | 58 | 0.33 | 178 |
|  | HIV-2 | 54 | >200 | <1 |
| AZT | HIV-1 | >1 | <0.008 | >125 |

In this field of study, it is considered that any compound exhibiting a Selectivity Index of greater than 5 has the potential for further study.

Other compounds considered significant are:

3,3'-(bis-1,5,9,13-tetraaza cyclohexadecane)

3,3'-(bis-1,5,8,11,14-pentaazacyclohexadecane), methylene (or polymethylene) di-1-N-1,4,8,11-tetraaza cyclotetradecane 3,3'-bis-1,5,9,13-tetraazacyclohexadecane 3,3'-bis-1,5,8,11,14-pentaazacyclohexadecane 5,5'-bis-1,4,8,11-tetraazacyclotetradecane 2,5'-bis-1,4,8,11-tetraazacyclotetradecane 2,6'-bis-1,4,8,11-tetraazacyclotetradecane 11,11'-(1,2-ethanediyl)bis-1,4,8,11-tetraazacyclotetradecane 11,11'-(1,2-propanediyl)bis-1,4,8,11-tetraazacyclotetradecane 11,11'-(1,2-butanediyl)bis-1,4,8,11-tetraazacyclotetradecane 11,11'-(1,2-pentanediyl)bis-1,4,8,11-tetraazacyclotetradecane 11,11'-(1,2-hexanediyl)bis-1,4,8,11-tetraazacyclotetradecane The active compounds may be administered in the form of pharmaceutical compositions formulated according to well known principles and incorporating the compound, preferably in unit dose form, in combination with a pharmaceutically acceptable diluent or excipient. Such compositions may be in the form of solutions or suspensions for injection, or irrigation or be in capsule, tablet, dragee, or other solid composition or as a solution or suspension for oral administration or formulated into pessaries or suppositories or sustained release forms of any of the above or for implantation. Suitable diluents, carriers, excipients and other components are known. It may be desirable also to formulate a composition for topical administration such as an ointment or cream. The compounds of the invention may be used, in the form of a composition or alone, and possibly carried on a finely divided support, as a coating on devices which in use contact body fluids, to discourage transmission of viral infections. Examples of devices to be considered in this aspect of the invention are surgical devices and gloves and contraceptives such as condoms, and other items, appliances, wound dressings and coverings, implements etc generally to be considered as devices according to this aspect of the invention.

The pharmaceutical compositions according to the invention may contain unit dosages determined in accordance with conventional pharmacological methods, suitably to provide active compounds in the dosage range in humans of from 0.1 to 100 mg/kg body weight per day, in a single dose or in a number of smaller doses. Preferred dosage ranges are 1 to 30 mg/kg body weight per day.

We claim:

1. A pharmaceutical composition which is active against HIV-infected cells in in vitro tests comprising, as active ingredient, a compound selected from the group consisting of bicyclam 3,3'-bis-1,5,9,13-tetraazacyclohexadecane 3,3'-bis-1,5,8,11,14-pentaazacyclohexadecane 5,5'-bis-1,4,8,11-tetraazacyclotetradecane 2,5'-bis-1,4,8,11-tetraazacyclotetradecane 2,6'-bis-1,4,8,11-tetraazacyclotetradecane 11,11'-(1,2-ethanediyl)bis-1,4,8,11-tetraazacyclotetradecane 11,11'-(1,2-propanediyl)bis-1,4,8,11-tetraazacyclotetradecane 11,11'-(1,2-butanediyl)bis-1,4,8,11-tetraazacyclotetradecane 11,11'-(1,2-pentanediyl)bis-1,4,8,11-tetraazacyclotetradecane 11,11'-(1,2-hexanediyl)bis-1,4,8,11-tetraazacyclotetradecane and a pharmaceutically acceptable carrier therefor.

2. A composition as claimed in claim 1, wherein the active ingredient is 2,2'-bicyclam.

3. A composition as claimed in claim 1, wherein the active ingredient is 6,6'-bicyclam.

* * * * *